Dec. 20, 1955 J. D. BROWNELL Plant Pat. 1,439
ROSE PLANT
Filed April 21, 1954
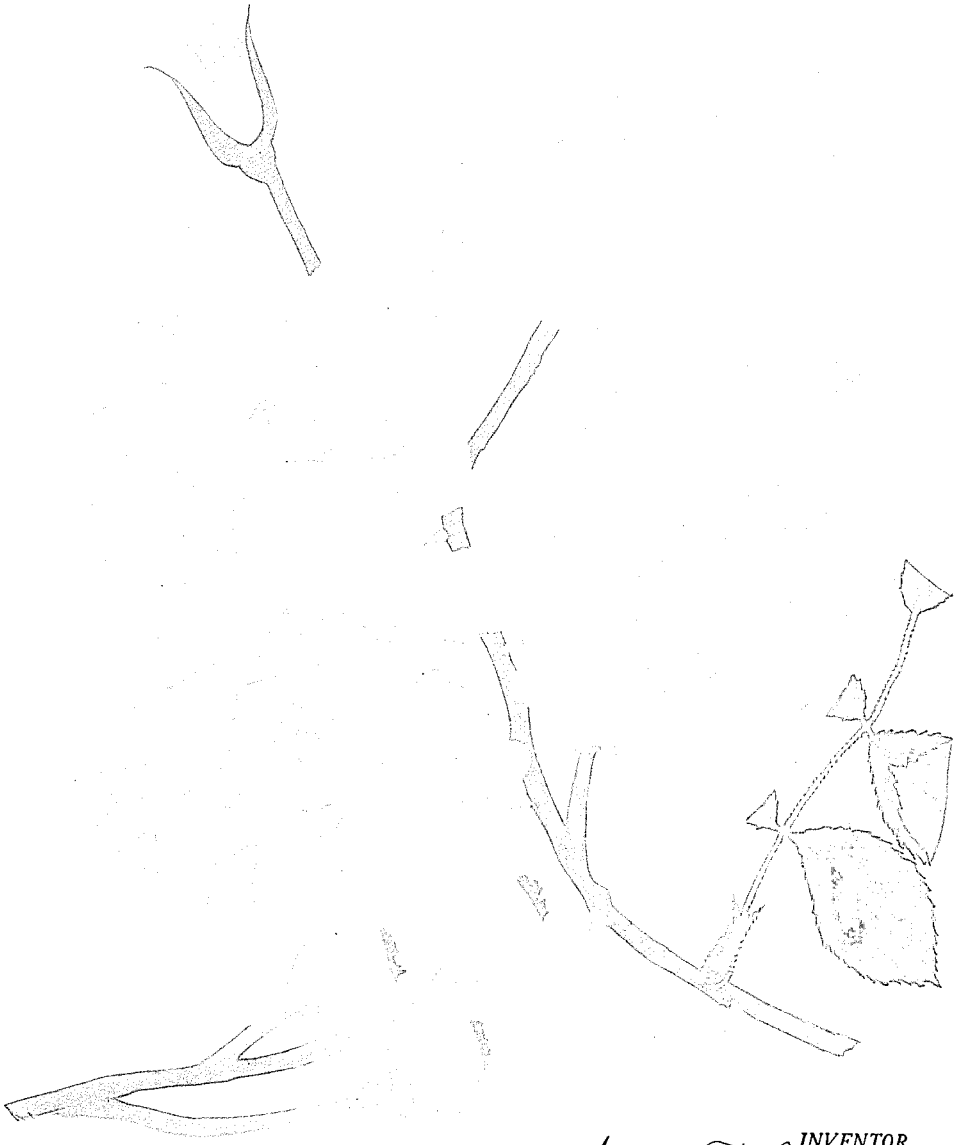
INVENTOR,
Josephine D. Brownell.

United States Patent Office

Plant Pat. 1,439
Patented Dec. 20, 1955

1,439

ROSE PLANT

Josephine D. Brownell, Little Compton, R. I.

Application April 21, 1954, Serial No. 424,792

1 Claim. (Cl. 47—61)

My invention relates to roses and especially to a new, original and distinct variety of the class known commercially as "everblooming climbers" and is a variant in that class, being a *Rosa wichuraiana* hybrid tea hybrid, in combination with cane growth usually common to climbing roses only, except the canes of my new rose usually bear terminal flowers and recurrent blooms on branches therefrom, often the same year that the canes grow, produced by me and under my direction in the breeding grounds of my research gardens in Little Compton, Rhode Island, by selection of variety variations and by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States;

The light yellow and pink shades (ordinary dictionary definition) of its petals, in combination with the unique brilliance thereof and their tendency to hold these colors under exposure;

The novelty and variation within certain definite limits of the form of the bloom, its character of holding that form for a long time and the petallage of the flowers;

Its character of fragrance;

Its unusual abundance of flowers, notable after early bloom time and until frost;

The intensity of its remontant and everblooming or reblooming character;

Its character of ascending in height by recurrent branching and progressively longer stems from the base, and by canes and cane branches therefrom.

The character of producing many seven leafleted leaves.

And especially its characteristic of freedom from premature defoliation by blackspot, under certain definite conditions of exposure, without any cultural control.

In the accompanying drawing forming a part of this specification I have shown my new rose in its natural colors; that is, as near as is possible to do so artificially.

The cluster pictured represents a cluster of blooms at the terminal end of a cane growth as it blooms the same season as the growth of the cane.

My new rose is otherwise described as follows:

ESSENTIAL INFORMATION

*Type*

Everblooming, *Rosa wichuraiana* hybrid, ascending to tall as climber, for garden display, cut flower and forcing or growing under glass.

*Class*

Hybrid tea crossed with *Rosa wichuraiana*, further restricted by originator to include only those varieties that can survive moderately low sub-zero temperatures.

*Breeding*

This variety was produced and bred by me and under my direction by cross pollination, selection and propagation.

It came into being as a seedling grown from a seed born on a plant of an unnamed seedling not patented and the pollen parent was Queen o' the Lakes, Plant Patent No. 1003.

The pollenation that fertilized the seed that grew into my new rose, as well as the two previous pollenations that produced its two parents, were directed by me and were performed by emasculating flowers and placing thereon a bag protecting from self and foreign pollen. These bags were later removed and the flowers were hand pollenated with a camel's hair brush and the bags immediately replaced. The date of the pollenation of my new rose was July 11 1949.[1] The seed was planted for me and under my direction on December 23, 1949, and the date of the first flower was July 29, 1950.

The plant and flower seemed to me to be of unusual merit and I have since made and directed extensive propagations and tests thereof.

Plants of this variety budded from this seedling on to *Rosa multiflora* root stock, have after been exposed to moderate sub-zero temperatures, survived and bloomed normally the following season in the hybrid tea manner. The variety has been propagated by budding at Little Compton, Rhode Island, in the months of July and August 1951 and 1952 and the characters have successively reproduced, true to the original seedling.

FLOWER

*Habit*

It blooms out of doors in Little Compton, beginning about three days prior to the average beginning time of commercial hybrid teas and continues relative to growth of the plant until frost.

*Flowers borne*

Often one and frequently two or three and occasionally more on each stem, in the usual hybrid tea type of cluster. And frequently more on climber canes as they mature. Such canes usually terminate in one or more blooms or clusters of blooms.

All of the foregoing bloom expression usually obtains the first year after budding on maidens and on two year old plants the first growing season after being transplanted.

The routine performance thereof is usually as follows. The plant first blooms like a hybrid tea, followed by cane growths, in length from about four to five feet, later more in length terminating in blooms. The hybrid tea growth continues to grow re-bloom stems in the hybrid tea manner until frost, also similar stems from the cane growths.

Occasionally cane growth will grow from the hybrid tea growth.

The canes seek to grow at an angle of about 85° from the horizontal.

The hybrid tea growth can usually be differentiated from cane growth by the diameters thereof and otherwise by characteristics common to each.

The pedicels and peduncles on the hybrid tea stems are medium in diameter and medium in length, erect, stiff, almost smooth, free from large prickles and bristles, on the cane ends usually wider diameter. Stems are long, diameter medium to small and notably stiff and rigid.

*Quantity of bloom*

Free, being cumulative in quantity from year to year as the plant increases in size, flowering through the summer and fall.

[1] This and other dates herein are approximate.

*Fragrance*

Distinctive, moderate and pleasing china tea in combination with that of *Rosa wichuraiana*, under favorable environment.

*Bud*

Neck as described, opens well, being little to not at all affected by hot or wet weather or both, as to color and form, except at very high temperatures the color is less intense and the form of the petals is less recurled.

Before the calyx breaks the size is medium, form high pointed, the sepals are usually normal and regular, tapering to lanceolate at their apex, usually without foliaceous appendages, turning back nearly perpendicular to the pedicel as the bud opens, usually no spurs on sides.

Color of the bud as the calyx opens, both sides of petals Lemon Yellow 4/2 and 4/3. Petals, both sides slightly stained and splashed and overlaid variously with Crimson at 22/2 and 22/3; color reference to English Horticultural Color Chart.[2]

*Bloom*

Color softens slowly to Lemon Yellow at 4/3 and later lighter, and the stains and splashes to 22/3 and lighter.

Color slightly variable dependent upon quality of sun.

The flower usually varies in size between three and four inches in diameter when fully open, petals average around between 12 and 19 occasionally less, including some smaller petals and petaloids in the center, variable in number.

The flower opens high centered, informal, and in its latest stages displays stamens and pistils. My new rose has an unusual characteristic in that, in its early opening stages does not display its pistils and anthers even though the outer petals are wide open. The petals are variable from obovate to ovate to irregular and frequently with surfaces variously slightly warped and edges especially of the smaller petals frequently notably irregular. Texture is medium to thick; both sides brilliant. The time of opening in favorable conditions is one to three days.

The petals are substantial and after about five days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

*Reproductive organs*

Stamens, quantity variable, medium long of slightly uneven length.

Anthers, nearly Marigold Orange at 11/3. Filaments, nearly Tangerine Orange at 9/3. Number variable around 45.

Pistils are several of nearly even length, averaging about one-half inch long, about 25 in number.

Sepals are persistent and break off easily.

PLANT

*Foliage*

Is abundant, of compound leaves of three to five leaflets near the flower, five leaflets lower down the stem and frequently seven leaflets in the middle of the stems and canes and nearer the base. Size of leaflets medium. Form of leaflets usually ovate with apex moderately acute, base rounded to slightly pointed in some instances with the circumference on one side of the petiolule out of alignment with the other side by about one-sixteenth of an inch or less, margins with slightly irregular small pointed serrations, petiolules short and wide at the base.

[2] Other color references to same unless otherwise indicated.

The leaflets average in width about one-half of their length.

Color of leaflets on the upper surface is slightly variable from Scheeles Green at 860, irregularly shaded with Spinach Green at o960/1, with reverse side nearly Asphodel Green frequently overlaid with trace of Dahlia Carmine, the color reference in this paragraph are to Robert Ridgway Color Standards.

The rachises are medium, moderately narrow to slender, upper side smooth except some very short hairs on edges. Under side moderately smooth, usually three to five short prickles.

Stipules are medium in length, with sharp points, the upper edges of which normally form an angle of about 90 degrees.

Habit, tall, upright, compact, climbing by canes and more cumulative in growth from year to year than the average climbing rose plant, and with canes that branch from canes and also by canes from the base. The growth is moderately free at first, developing more rapidly after one or two years under favorable vegetative opportunity.

Color of mature stems is Scheeles Green at 860/3, shading variously lighter.

Prickles, several, frequently two to five between leaves, averaging in length a little more than one-quarter inch, shading from Crimson at 22 to lighter at the base, turning lighter throughout and later to nearly colorless.

*Winter resistance*

A notable characteristic of this new rose is the resistance to moderate sub-zero temperatures in combination with its everblooming character, its climbing habit and its *Rosa wichuraiana* ancestry. The word temperature herein refers to the Farenheit scale.

*Comparisons*

This rose variety is one of a new race or type of rose, not found in nature or in commerce, produced by combining by mutation in certain of its anticedents and by breeding several varieties containing different variations of floral expression, and using such resultant material as breeders. The fact of this mutational involvement has obtained is evidenced by the following facts: The combination can only obtain by mutation. We have made crosses here to the extent upward of one million, in which such combination has not obtained. When it obtains it comes into being usually in the field or the garden on a plant which normally produces roses, either in the once bloom class or the everblooming class. It can on occasion be detected by observation and found to reproduce that mutation by asexual reproduction, that has been the case of my new rose.

One of the varieties somewhat resembling my new rose is Betty Prior, not patented, which lacks some of the Hybrid Tea type of rebloom expressed by my new rose, and does not climb.

I do not believe there is any rose variety closely resembling my new rose.

The climbing rose Doctor J. H. Nicholas, Plant Patent No. 457, is perhaps the nearest, this variety has blooms with more petals, and does not bloom on canes at their terminal end as they mature as does my new rose.

I claim:

The new and distinct variety of rose plant as described and illustrated, characterized by its color pattern, fragrance, form and Lemon Yellow and Crimson color of its blooms at the terminal end of canes that bloom the same season in which the canes grow; also, by the Wichuraiana, hybrid tea, and everblooming climber characteristics, substantially as described.

No references cited